United States Patent
Lu et al.

(10) Patent No.: US 9,186,421 B2
(45) Date of Patent: Nov. 17, 2015

(54) ESTABLISHMENT OF RHESUS MONKEY MODEL OF AUTOIMMUNITY TYPE 1 DIABETES

(75) Inventors: Yanrong Lu, Chengdu (CN); Jingqiu Cheng, Chengdu (CN); Shaoping Deng, Chengdu (CN); Younan Chen, Chengdu (CN); Bole Tian, Chengdu (CN); Gang Mai, Chengdu (CN); Yan Ren, Chengdu (CN); Li Wang, Chengdu (CN); Hongxia Li, Chengdu (CN); Lingling Wei, Chengdu (CN); Xi Jin, Chengdu (CN); Chaofeng Qiao, Chengdu (CN); Wensheng Zhang, Chengdu (CN); Sirong He, Chengdu (CN); Li Zeng, Chengdu (CN)

(73) Assignee: West China Hospital, Sichuan University, Sichuan (CN)

( * ) Notice: Subject to any disclaimer, the term of this patent is extended or adjusted under 35 U.S.C. 154(b) by 34 days.

(21) Appl. No.: 13/637,125

(22) PCT Filed: Mar. 26, 2010

(86) PCT No.: PCT/CN2010/000378
§ 371 (c)(1),
(2), (4) Date: Nov. 30, 2012

(87) PCT Pub. No.: WO2011/116501
PCT Pub. Date: Sep. 29, 2011

(65) Prior Publication Data
US 2013/0149733 A1 Jun. 13, 2013

(51) Int. Cl.
*A01K 67/00* (2006.01)
*A61K 49/00* (2006.01)
*A01K 67/027* (2006.01)

(52) U.S. Cl.
CPC ........... *A61K 49/0008* (2013.01); *A01K 67/027* (2013.01); *A01K 2207/20* (2013.01); *A01K 2227/106* (2013.01); *A01K 2267/0362* (2013.01)

(58) Field of Classification Search
CPC ...................... Y10S 514/866; A01K 2227/108; A01K 2267/03; A01K 67/027; C12Q 1/6883; C12Q 2600/18; C12Q 2600/158
See application file for complete search history.

(56) References Cited

FOREIGN PATENT DOCUMENTS

WO    WO 2008010690 A1 *   1/2008

OTHER PUBLICATIONS

Qiao et al. Induction of Diabetes in Rhesus Monkeys and Establishment of Insulin Administration Strategy. Transplantation Proceedings, 2009. 41:413-417.*
Koulmanda et al. The Effect of Low Versus High Dose of Streptozotocin in Cynomolgus Monkeys (*Macaca fascilularis*). American Journal of Transplantation, 2003. 3:267-272.*
Lu et al, The Evidences of Induced Autoimmue Diabetes in Primates: Establishment of a Preclinical Large Animal Model of T1DM. Abstract. Xenotransplantation, (Sep.-Oct. 2009) vol. 16, No. 5, pp. 348. Abstract No. JOINT-O-1.5. Meeting Info: 2009 Joint Meeting of the International Pancreas and Islet Transplant Association (IPITA) and the I.*
Elias et al. Autoimmune Diabetes Induced by the Beta-Cell Toxin STZ. Diabetes, 1994. 43: 992-998.*
El-Housseiny et al. Studies on the Induction of Stable and Prolonged Hyperglycemia by SubDiabetogenic Dose of Streptozotocin (STZ). Journal of Drug Research, Egypt, 1987. 17(1-2): 45-51.*
Jones et al. Streptozotocin Diabetes in the Monkey: Plasma levels of Glucose, Insulin, Glucagon, and Somatostatin, with Corresponding Morphometruc Analysis of Islet Endocrine cells. Diabetes, 1980. 29(7)536-46. Abstract only.*
Wright et al, Synergistic Effect of Adjuvants, Endotoxin, and Fasting on Induction of Diabetes With Multiple Low Doses of Streptozocin in Rats. Diabetes, 1998. 37(1):112-118.*
Gaur, Lakshmi K. Nonhuman Primate Models for Islet Transplantation in Type 1 Diabetes Research. ILAR Journal, 2004. 45(3):324-333.*

* cited by examiner

*Primary Examiner* — Maria Leavitt
*Assistant Examiner* — Kimberly A Aron
(74) *Attorney, Agent, or Firm* — Cesari and McKenna, LLP

(57) ABSTRACT

Use of low dose streptozocin in the preparation of an animal model for screening drugs for treatment of antoimmune type 1 diabetes is disclosed, in which streptozocin is administrated intravenously at a dose of 15-30 mg/kg per time for 5 days and administrated again on the $7^{th}$ day and $14^{th}$ day after last time of offering drug. A method for preparing rhesus monkey model of autoimmune type 1 diabetes and autoimmune type 1 diabetes animal model obtained are also disclosed.

3 Claims, 2 Drawing Sheets

ESTABLISHMENT OF RHESUS MONKEY MODEL OF AUTOIMMUNITY TYPE 1 DIABETES

CROSS-REFERENCE TO RELATED APPLICATIONS

This application is the National Stage of International Application No. PCT/CN2010/000378, filed on Mar. 26, 2010. The content thereof is hereby incorporated by reference in its entirety.

FIELD OF THE INVENTION

The present invention relates to a method of preparing a rhesus monkey model of autoimmune type 1 diabetes.

BACKGROUND OF THE INVENTION

The etiology of autoimmune type 1 diabetes is unknown and no effective prevention method has been developed yet. While the common insulin treatment may regulate blood glucose levels to some extent, but long-term use cannot control the occurrence of complications of diabetic effectively, and some patients may encounter hypoglycemia shock. How to prevent autoimmune attack on islet β cells and develop effective β cell transplantation treatment has become a crucial issue in diabetes research.

At present, rodents are the most commonly used animal models in diabetes study. Since rodents are far away from human beings on the evolutionary relationships, the experimental data obtained by studying them have little clinical significance. Rhesus monkey has the similar anatomical characteristics, physiological functions of various systems, and response to diseases and drugs to human beings and is a sensitive animal for evaluating preclinical efficacy and safety of immunological-related treatments, stem cell transplantation, and heterotransplantation. The use of rhesus diabetes model for evaluation of new diabetes drugs and study of immune rejection mechanism and transplantation tolerance induction of islet stem cells and islet heterotransplantation is an internationally recognized pre-clinical experimental system, which has important guiding significance to future clinical application of these treatment programs. Therefore it is an urgent demand to establish a non-human primate model of diabetes for the islet (stem) cell transplantation research and preclinical drug evaluation.

Now the commonly used diabetes animal models include experimental diabetes animal model and spontaneous diabetes animal model. The spontaneous model has higher application value, but cannot be widely used due to low incidence, expensive cost, strict feeding and breeding conditions. Experimental model is used more widely and commonly used induction methods include pancreatic resection, chemical drug induction, virus infection, antagonizes insulin factor, food induction and fattening. Chemical drug induction method is highly thought of by many researchers due to its simple operation and high feasibility; however, in these methods streptozotocin has relatively small toxicity to body tissues and allowing animals have high survival rate, and is more widely used for preparing animal model of diabetes at home and abroad.

Streptozocin (STZ) is an induced reagent that is commonly used for preparing models of diabetes, which has selective destruction of pancreatic β cells of certain animal species, making many animals develop diabetes and the most commonly used of streptozocin is in rat model. Common induction method is as follows: the rats are fasted for 12 h and intraperitoneally injected with 60 mg/kg body weight of STZ once a day for two consecutive days to prepare a rat model of type 1 diabetes successfully. And such model has the characteristics of high blood glucose, mitigated weight, polydipsia, polyphagia and polyuria, which are consistent with the clinical type 1 diabetes; however, in this experiment, when the model is injected intraperitoneally with STZ only once and fed with high calorie feed for 12 weeks, then the model prepared is an animal model of type 2 diabetes, and the model prepared by such method has the characteristics of overweight, reduced glucose tolerance, elevated blood lipids, elevated serum insulin and reduced insulin receptor binding along with insulin resistance, which are similar to the clinical features of patients with type 2 diabetes. The preparation of animal models of type 1 diabetes and type 2 diabetes may be related to the injection dose of STZ: when injected with high dose of STZ (usually 120 mg/kg), due to the directly extensive destruction of pancreatic β cells, type 1 diabetes model is prepared; when injected with low dose of STZ, partial function of pancreatic β cells is destroyed, causing peripheral tissue not to be sensitive to insulin. Meanwhile high calorie feed is given. The combination of two conditions induce an animal model, the pathological and physiological changes of which are close to that of human type 2 diabetes. Therefore, the dose of STZ directly determines the type of the diabetic animal model prepared.

Establishment of rhesus monkey model of diabetes with STZ has been reported in some references, such as: KUANG De-xuan, et al. (Effect of Different Dosage of Streptozotocin on Some Physiological Data in Rhesus Monkey, *Acta Lab Anim Sci Sin*, March, 2003, Vol. 11, No. 1) studied the physiological data of food and water intake, urination, body weight, plasma glucose and glycosuria with streptozotocin (STZ) in rhesus monkeys, which was essential to establish animal model for diabetes. Methods: Seven rhesus monkeys were injected intravenously with different doses of STZ. The administration dose and method of STZ are as follows: low dose of 30 mg/kg, with an interval of 15 days, repeatedly injected for once to twice; mild dose of 45 mg/kg, injected with STZ once; high dose of 60 mg/kg, injected once. Experimental results: The seven monkeys showed the same clinical features as those of diabetes patients at a different time and extent, such as polyphagia, polydipsia, polyuria, hyperglycosuria, body weight loss. The clinical characteristics were lightened and controlled by using insulin. Especially the clinical symptoms of mild-dose and high-dose of STZ were more obvious than those of low-dose in monkeys. The body weight of low-dose monkeys rose in a short time, then dropped rapidly. Plasma glucose and glycosuria of monkeys were increased with STZ injected, especially mild-dose and high-dose monkeys varied obviously. Thus, the acute animal model similar to human diabetes was induced by mild-dose and high-dose of STZ (45-60 mg/kg). The course of animal model of diabetes may be extended by using insulin treatment or low-dose of STZ, which is suitable for studying complications of diabetes. Biochemical changes in rhesus monkey during the first days after streptozotocin administration are indicative of selective beta cell destruction, Takimoto G, Jones C, Lands W, Bauman A, Jeffrey J, Jonasson O., *Metabolism*. 1988 April; 37(4): 364-70. 22 rhesus monkeys were selected and injected intravenously with STZ (45 to 55 mg/kg). Almost half of the monkeys developed insulin-dependent diabetes within five days after injection. Four of the remaining monkeys did not become insulin dependent for at least 6 months after STZ administration, during which time they were considered non-insulin-dependent, and the remaining eight monkeys never required exogenous insulin.

Autoimmune diabetes may be divided into diabetes in children and adolescents and latent autoimmune diabetes in adults (LADA), which are subtypes of type 1 diabetes. They have the characteristics as follows: 1) Diabetes in children occurs at age under 15 years old, while LDAD may occur at any age over 15 years old. They are not insulin-dependent within half of a year after outset and have no ketosis; 2) Most patients are non-obese at the outset of diabetes; 3) Islet B cell antibodies in vivo (such as ICA, GAD and insulin autoantibodies) are always positive; 4) They have predisposing genes of type 1 diabetes (such as HLA-DR3, HLA-DR4, BW54 and DQ-131-57-Non-Asp); 5) They are often accompanied by specific antibody positive of organs such as thyroid and gastric parietal cells. Once diagnosed as LDAD, insulin treatment should be applied in early stage to protect the relict β cells. The information about patients in Europe and the United States shows that LADA accounts for about 10%-15% of type 2 diabetes, and the ratio was up to 50% in non-obese patients with type 2 diabetes. It is reported that the positive rate of GAD-Ab in patients with type 2 diabetes is 14.2%. The cause of this type is insulin deficiency caused by autoimmune destruction of islet β cells. Markers of the autoimmune process include lymphocytic infiltration of pancreatic islets and pancreatic islet cells autoantibodies, islet cell antigen autoantibodies, and detection of insulin autoantibodies.

While the reference has reported that rhesus monkey animal model of insulin-dependent diabetes could be induced by mild-dose and high-dose of STZ (45-60 mg/kg), primate animal models of autoimmune type 1 diabetes prepared by low dose of STZ (less than 30 mg/kg) has not been reported yet.

SUMMARY OF THE INVENTION

One aspect of the present invention is to provide a use of low dose of streptozotocin in the preparation of an animal model for screening drugs for treatment of autoimmune type 1 diabetes. Another aspect of the present invention is to provide the establishment of rhesus monkey model of autoimmune type 1 diabetes.

The present invention provides a use of low dose streptozocin in the preparation of an animal model for screening drugs for treatment of autoimmune type 1 diabetes, in which streptozocin is administrated intravenously at a dose of 15-30 mg/kg per time.

Wherein the administration method and dose of streptozotocin are as follows: streptozotocin is administered intravenously at a low dose of 15-30 mg/kg per time for 5 consecutive days and administrated again on the $7^{th}$ day and $14^{th}$ day after last administration. More preferably, streptozotocin is administered at a dose of 20-25 mg/kg.

The present invention also provides a method of preparing an animal model of autoimmune type 1 diabetes, comprises administering streptozotocin into a primate, wherein streptozotocin is administered intravenously at a dose of 15-30 mg/kg per time.

Wherein said primate is rhesus monkey.

Wherein the administration method and dose of streptozotocin are as follows: streptozotocin is administered intravenously at a low dose of 15-30 mg/kg per time for 5 consecutive days and administrated again on the $7^{th}$ day and $14^{th}$ day after last administration.

The present invention also provides an animal model of autoimmune type 1 diabetes prepared by the above method.

The present invention also provides a use of the above animal model for screening drugs for treatment of autoimmune type 1 diabetes.

The present invention also provides a method of screening drugs for treatment of autoimmune type 1 diabetes, comprising the steps of:

a) administering streptozocin into a primate at a dose of 15-30 mg/kg per time;

b) administering a candidate into the primate of step a);

c) evaluating the potential drug for treatment of autoimmune type 1 diabetes using the animal model of autoimmune type 1 diabetes.

Wherein said primate in step a) is rhesus monkey. The administration method and dose of streptozotocin are as follows: streptozotocin is administered intravenously at a low dose of 15-30 mg/kg per time for 5 consecutive days and administrated again on the $7^{th}$ day and $14^{th}$ day after last administration.

Wherein said evaluation in step c) mainly includes the following indexes: onset time, incidence rate of diabetes and damage degree of n-cells of an animal.

The animal model of the present invention can be used to evaluate new bio-technology drugs and evaluate stem cell transplantation treatment technology, which cannot be achieved by rodent models.

The following embodiments are used to describe the present invention in detail, and should not be construed in any way as limiting the present invention. Various modifications and variations, which may be made by those skilled in the art without departing from the spirit of the present invention, are also encompassed by the accompanying claims of the present invention.

DESCRIPTION OF THE DRAWINGS

FIG. 1B: negative control; FIG. 1C: test results of serum anti-islet cell antibody of animal model (ID: 05539) of the present invention; FIG. 1D: test results of serum anti-islet cell antibody of animal model (ID: 05572) of the present invention), scale bar is 50 µm.

FIG. 2B: pancreas of animal model of the present invention: lymphocytic infiltration was observed around the islet (scale bar is 50 µm); FIG. 2C: anti-CD3 monoclonal antibody immunohistochemical staining: T cell infiltration was mainly observed).

FIG. 3B: distribution of glucagon-expressing cells) (scale bar is 100 µm)).

DETAILED DESCRIPTION OF THE INVENTION

Example 1

Figure 1:
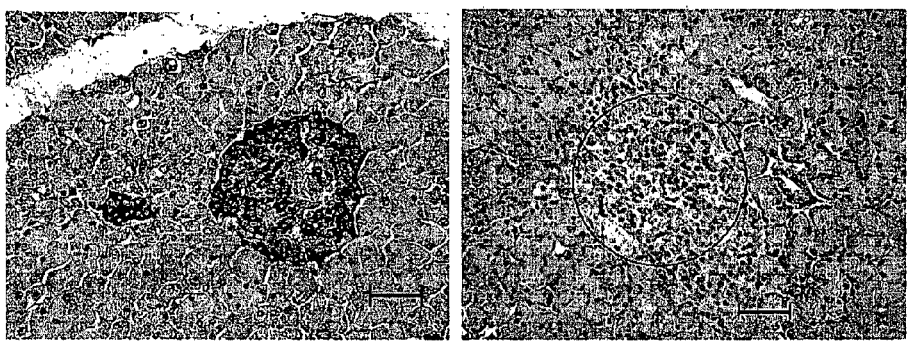
FIG. 1 shows the test results of serum anti-islet cell antibodies (wherein FIG. 1A: positive control of anti-insulin antibodies.
Figure 1:

Preparation of Animal Model of the Present Invention

1. Materials and Methods:
1.1 Materials 6 female and male rhesus monkeys, 2 to 3-year-old, without B herpes virus, monkey retroviruses, monkey leukemia virus and immunodeficiency virus infection; purchased from Pingan Animal Breeding and Research Base (Chengdu, China).

1.2 Main Reagents

Streptozotocin (STZ): purchased from Chengdu Yuyang High-Tech Development Co., Ltd. (China).

Other drugs and materials were purchased from Likang Pharmacy of West China Hospital.

1.3 Preparation of main solutions

Preparation of Streptozocin Solution:

Preparation of 0.1 mol/L sodium citrate buffer:

A solution (0.1 mol/L citrate solution): 2.1g of citrate ($C_6H_8O_7 \cdot H_2O$ FW: 210.14) was taken and dissolved in 100 ml of double distilled water. B solution (0.1M sodium citrate solution): 2.94 g of sodium citrate ($C_6H_5Na_3O_7 \cdot 2H_2O$ FW: 294.10) was dissolved in 100 ml of double distilled water.

Working solution: When needed, 28 ml of A solution and 22 ml of B solution (in a ratio of 1.32:1) were taken, diluted to 100 ml with double distilled water, and adjusted to pH=4.5.

Streptozotocin solution: STZ was taken according to the weight ratio of the animals, and dissolved with the above A and B mixed working solution at a concentration of 1%. It was prepared immediately before its use. The solution should be prepared and stored at 4° C. and injected within 30 minutes.

1.4 Main Instruments

1) Anesthesia machine: Excel 210 SE, Datex-OHMEDA

2) Ventilator with ECG monitor: M/206B, Philips Company

3) High frequency electrotome (H.F.ELECTROTOME): Type GD-350-P, Shanghai Hutong Electronics Co., Ltd. (China)

4) Blood glucose monitor: Rocand full vigor type blood glucose meter, Rocand full vigor blood glucose test strips.

5) Full wavelength spectrophotometer 1.5 Experimental Methods 1.5.1 Intravenous Glucose Tolerance Test of Rhesus Monkey The intravenous glucose tolerance test (IVGTT) was performed to measure animal pancreatic function, understand the fluctuation range of blood glucose, and exclude the possibility of spontaneous diabetes of the animals.

1) The animals were fasted for 10-12 hours but may have water;

2) The animals were intramuscularly injected with 15 mg/kg of ketamine (50mg/ml) according their body weight when purchased;

3) After the animals were anesthetized, their body weight was accurately measured and recorded;

4) Upper and lower extremities of the rhesus monkeys were fixed on an operating table. Posterior legs of lower extremities were subjected to skin preparation to expose great saphenous veins, which were disinfected with iodine and fluorine;

5) The great saphenous veins were punctured with a 20 G indwelling needle. 6 ml of blood was collected with a 5 ml syringe (which was used for biochemical test, routine blood test, blood glucose test and fasting insulin test, designated as a value at 0 minute);

6) The animals were intravenously injected with 0.5 g/kg of 50% glucose hypertonic solution with a 5 ml syringe immediately (within 30 seconds), meanwhile timing began; then injected with 5 ml of saline, and 1 ml of heparin into the indwelling needle (250 U/ml).

7) 1.5 ml of blood samples were taken at 1, 3, 5, 10, 30 minutes, respectively and placed into red head blood collecting tubes to measure insulin levels. Meanwhile, blood glucose levels were measured at 0, 1, 3, 5, 10, 30, 60, 120 minutes, respectively.

8) After the completion of measurement, the animals were taken back to the cages and observed until waking up.

1.5.2 Diabetes model prepared by low dose STZ induction

Low dose of STZ was administered intravenously for 5 consecutive days, at a dose of 15-30 mg/kg per time; and administrated again on the $7^{th}$ day and $14^{th}$ day after last administration. Fasting glucose was observed once each week. The model was considered to be established successfully when fasting glucose levels were higher than 11.1 mmol/L and C-peptide levels were less than 0.3 nM, as well as anti-islet cell antibody and anti-insulin antibody were positive for 2 consecutive days.

The administration dose regimens for two groups of experimental animals are as follows:

| | Dose of STZ (mg/kg) | | | | | | |
|---|---|---|---|---|---|---|---|
| | Day 1 | Day 2 | Day 3 | Day 4 | Day 5 | Day 12 | Day 19 |
| Group 1 | 20 | 20 | 20 | 20 | 20 | 20 | 20 |
| Group 2 | 25 | 25 | 25 | 25 | 25 | 25 | 25 |

6 rhesus monkeys were used to prepare models according to the method of the present invention and 4 models were successfully prepared.

1.5.3 Determination of serum insulin of rhesus monkeys (radioimmunoassay):

Serum insulin levels of the animals were analyzed using insulin detection kits from Beijing North Institute of Biotechnology according to the operating instructions.

1.5.4 Determination of serum islet cell antibody (immunohistochemistry):

Normal monkey pancreas tissue slides were used to react with test group monkey serum, normal monkey serum (negative control) and anti-insulin antibodies (positive control), respectively, and then bind with HRP-labeled secondary antibodies. After adding chromogenic substrates, the staining condition of the islet cells was observed under a microscope to determine whether the anti-islet cell antibodies exist or not.

1.5.5 Determination of rhesus monkey serum insulin antibody (enzyme-Linked immunosorbent assay): Serum insulin antibodies of the animals were analyzed using insulin antibody detection kits from Beijing North Institute of Biotechnology according to the operating instructions.

1.5.6 Pancreas, liver and kidney biopsy surgery

1) The animals were subjected to basal anaesthesia with 15 mg/kg of ketamine (50 mg/ml), followed by weighing the body weight.

2) The animals were fixed on the operating table in a supine position. Skin preparation was performed on two lower extremities to establish intravenous access.

3) Skin preparation was performed around the surgical region, which was beneath the bilateral nipple line, above the groin, and in front of the anterior axillary line.

4) Intravenous anesthesia and tracheal intubation were performed through intravenous access. The ventilator and the anesthesia machine were used throughout the surgery, while ECG monitoring was performed. Oxygen saturation, respiration and body temperature were monitored; femoral artery channel was established to measure arterial blood pressure.

5) The surgical operator was subjected to hand disinfection and the surgical region was disinfected. The skin region radiated at least 15 cm around the surgical incision (median upper abdominal incision) was rubbed without omission with Eric gauze. After natural drying of the Eric solution (povidone iodine solution), it was wiped with cotton balls with 70% alcohol.

6) Sterile towel, sterile large drape and large surgical hole drape were laid. The upper end of the sterile large drape should overshadow the narcotic frame, and the lower end should overshadow the feet of the animals. The hole of the surgical hole drape was aligned to the operative skin.

7) An incision was cut at the median of upper abdominal. The skin at the incision was sterilized with 70% alcohol again before cutting, then skin, subcutaneous fat, muscle and peritoneum were cut sequentially to reach abdominal cavity.

8) Pancreas detection was performed. Gastrocolic ligament was cut off to get into the lesser omental cavity.

9) Acquirement of pancreatic biopsies tissue: 1 cm of pancreatic body and duodenum was bluntly dissected, the blood vessels of which were ligated with No.1 silk wire to cut off pancreatic tissue (about 0.5 g).

10) Acquirement of liver biopsies tissue: The liver lobe edge was subjected to ligation with No.1 silk wire and then wedge cutting to obtain about 1 g of tissue.

11) Acquirement of kidney biopsies tissue: The kidney edge was subjected to ligation with No.1 silk wire and then wedge cutting to obtain about 0.3 g of tissue.

12) The abdominal cavity was cleaned, and the abdominal incision was sutured layer by layer.

13) Surgery awaking and postoperative care: The animals were fasted for 1 day after surgery. They were injected intramuscularly with tramadol for pain relief within 24 hours after awakening from surgery, and administered with cefotaxime sodium for 5 days for anti-infection treatment.

14) Animal blood glucose was detected after surgery. Stitches were removed after 7 days, and biochemical blood routine examination was performed.

2. Experimental Results

Figure 2:
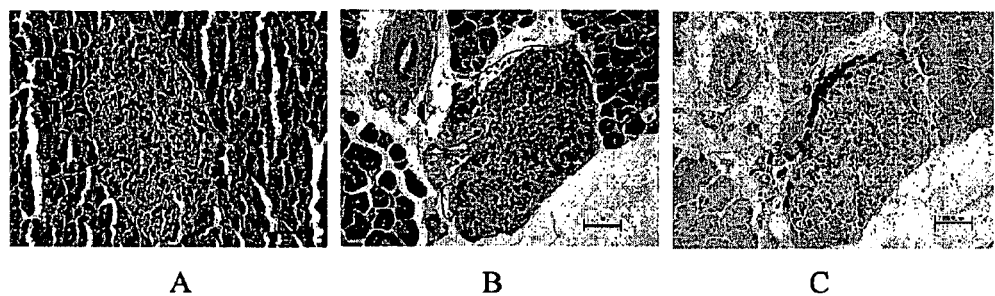
FIG. 2 shows the HE staining results of monkey pancreatic tissue slides (FIG. 2A: normal monkey pancreas (scale bar is 50 µm)
Figure 3:
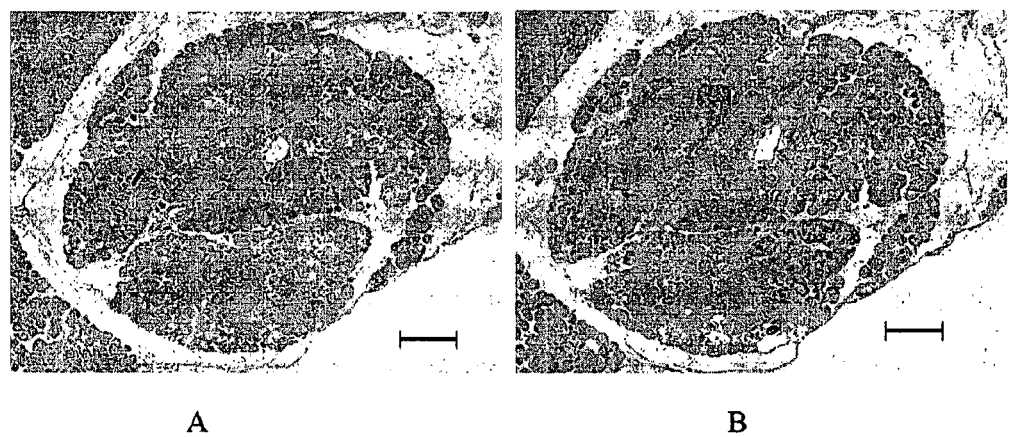
FIG. 3 shows the immunohistochemical results of pancreatic tissue slides of animal model of the present invention (FIG. 3A: distribution of insulin-expressing cells.

The fasting blood glucose of rhesus monkeys was fluctuated between 3.2-17.6 mmol/L after intravenous injection of STZ. The fasting blood glucose of the animals was consistently higher than 11.1 mmol/L, and the serum C-peptide detected was less than 0.3 nM; serum anti-islet cell antibodies (see FIG. 1C, 1D) and anti-insulin antibodies were detected as positive; animal pancreatic tissue biopsy showed that there was lymphocytic infiltration around the islet (FIG. 2B); anti-CD3 monoclonal antibody immunohistochemical staining showed there was mainly T-cell infiltration (FIG. 2C); There was only a very small amount of insulin expression-positive cells remained in the islet tissue (FIG. 3A), and above 90% of the cells were glucagon expression-positive cells (FIG. 3B). Thus, it is determined that an autoimmune type 1 diabetes model was established successfully.

Example 2

Pharmaceutical Intervention Trial of the Animal Model of the Present Invention

1. Tested drug: cyclosporine (an immunosuppressive drug, which can reduce the incidence of autoimmune diabetes in mice);

2. Test method: intervention effect of cyclosporine on the pathogenesis of autoimmune diabetes The experiment groups were divided into saline blank control group and cyclosporine intervention group. During the progress of STZ-induced autoimmune diabetes, the intervention group was administrated with cyclosporine (2.5 mg/kg) every day. The onset time and incidence rate of diabetes and damage degree of β cells between the control group and the intervention group were compared.

By interfering with the pathogenesis of autoimmune diabetes by an immunosuppressive drug, it was observed that the damage degree of β cells in the animal model was reduced, which further demonstrated that the animal model of the present invention was autoimmune type 1 diabetes model, and the model could be established successfully using the modeling approach of the present invention.

Example 3

Validation of Rhesus Animal Model of Autoimmune Type 1 Diabetes with a Drug for Treatment of Autoimmune Type 1 Diabetes and Preliminary Establishment of a Related Drug Screening Platform At present, insulin injection is the main treatment method of autoimmune type 1 diabetes. Insulin was applied to the rhesus monkey model of autoimmune type 1 diabetes in this experiment. The specific way was as follows:

1. According to the habit of eating twice per day of rhesus monkeys, different types of insulin were injected twice a day (9:30 am & 17:30 pm) in different doses, applied to the autoimmune type 1 diabetes model prepared by Example 1 of the present invention: combined treatment of (1) long-acting insulin: porcine insulin (protamine zinc insulin) produced by Wanbang Company (Xuzhou, China) and (2) short-acting insulin: ordinary porcine insulin produced by Wanbang Company (Xuzhou, China).

2. Initially, low dose of insulin (0.4 U/kg) was injected subcutaneously so as to avoid the occurrence of low blood glucose.

3. The fasting and postprandial glucose levels were monitored. The administration dosage was adjusted according to the blood glucose level, finally allowing the fasting and postprandial blood glucose to be less than 10 mmol/L and glycosylated hemoglobin to be less than 6.5%.

Experimental results: Insulin has a better therapeutic effect on autoimmune type 1 diabetes.

The experiment demonstrated that the animal model of the present invention is suitable for the treatment research of autoimmune type 1 diabetes and the occurrence and treatment research of complications of diabetes, and can be used for screening drugs and treatment methods of autoimmune type 1 diabetes.

In summary, the present invention establishes an animal model of autoimmune type 1 diabetes successfully, which can be used to evaluate new bio-technology drugs and evaluate stem cell transplantation treatment technology, which cannot be achieved by rodent models.

INDUSTRIAL APPLICABILITY

The present invention provides a use of low dose of streptozotocin in the preparation of an animal model for screening drugs for treatment of autoimmune type 1 diabetes, wherein streptozotocin is administered at a dose of 15-30 mg/kg per time. The animal model of the present invention can be used to evaluate new bio-technology drugs and evaluate stem cell transplantation treatment technology, which cannot be achieved by rodent models, and is suitable for industrial application.

What is claimed is:

1. A method of preparing a rhesus monkey model for screening drugs for treatment of autoimmune type 1 diabetes, the method comprising:

intravenously administering streptozotocin to a rhesus monkey at a dose of 20-30 mg/kg per injection per diem for 5 consecutive days, the first injection being given on day 1; and intravenously administering streptozotocin to the rhesus monkey at a dose of 20-30 mg/kg per injection per diem on the $12^{th}$ day and the $19^{th}$ day after day 1 of the 5-day administration, wherein the rhesus monkey exhibits a fasting glucose level greater than 11.1 mmol/L, a C-peptide level less than 0.3 nM, and has anti-islet cell antibodies and anti-insulin antibodies.

2. An autoimmune type 1 diabetes rhesus monkey model prepared by the method of claim 1, wherein the rhesus monkey exhibits a fasting glucose level greater than 11.1 mmol/L, a C-peptide level less than 0.3 nM, and has anti-islet cell antibodies and anti-insulin antibodies.

3. A method of screening drugs for treatment of autoimmune type 1 diabetes, comprising the steps of:
   a) administering a candidate drug into the rhesus monkey model of claim 2;
   b) evaluating the candidate drug for treatment of autoimmune type 1 diabetes.

\* \* \* \* \*